United States Patent [19]

Green et al.

[11] Patent Number: 4,982,734

[45] Date of Patent: Jan. 8, 1991

[54] ANAESTHESIA EQUIPMENT

[75] Inventors: Alan C. Green, Oxford; Richard Eeles, Bampton, both of England

[73] Assignee: Penlon Limited, United Kingdom

[21] Appl. No.: 346,795

[22] Filed: May 3, 1989

[30] Foreign Application Priority Data

May 7, 1988 [GB] United Kingdom ............... 8810873

[51] Int. Cl.$^5$ .......................................... A61M 16/00
[52] U.S. Cl. ..................... 128/200.14; 128/200.19; 128/205.24; 251/149.9; 251/89.5; 137/637.1; 137/614.06; 137/884; 74/483 K
[58] Field of Search ................ 128/202.27, 200.14, 128/200.19, 203.12, 205.24; 249/149.9, 143, 89.5; 137/637.1, 614.06, 884, 798; 74/483 K, 483 R

[56] References Cited

U.S. PATENT DOCUMENTS

| | | | |
|---|---|---|---|
| 2,835,251 | 5/1958 | Oliveau | 128/202.27 |
| 3,038,472 | 6/1962 | Gaylord | 128/202.27 |
| 3,185,148 | 5/1965 | Gaylord | 128/202.27 |
| 3,831,599 | 9/1974 | Needham | 128/203.12 |
| 4,308,865 | 1/1982 | Hay | 128/200.19 |
| 4,351,327 | 9/1982 | Rinne | 128/200.14 |
| 4,493,316 | 1/1985 | Mohr et al. | 128/200.19 |
| 4,759,358 | 7/1988 | Gregory | 128/200.14 |

FOREIGN PATENT DOCUMENTS

| | | | |
|---|---|---|---|
| 1385670 | 2/1972 | United Kingdom . | |
| 2052271A | 1/1981 | United Kingdom . | |
| 2177007 | 1/1987 | United Kingdom | 128/203.12 |

Primary Examiner—Eugene H. Eickholt
Attorney, Agent, or Firm—Stevens, Davis, Miller & Mosher

[57] ABSTRACT

Anaesthesia equipemnt comprising an anaesthesia unit such as a vaporizer detachably mounted on a mounting rack by connecting means comprising guide means to provide substantial leak-proof engagement of the connecting means.

The guide means may comprise an elongated pin or tongue mounted on the unit or rack to cooperatively engage an aperture groove or slot on the rack or unit respectively to substantially prevent movement of the unit towards or away from the rack when mounted thereon.

9 Claims, 3 Drawing Sheets

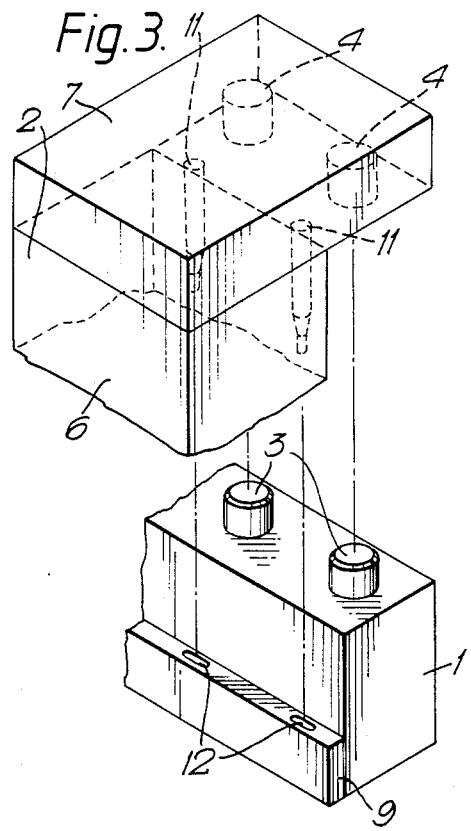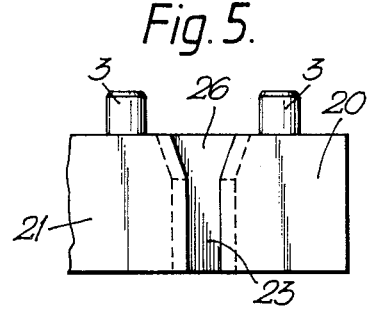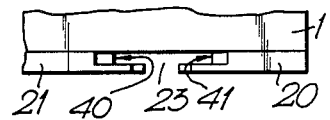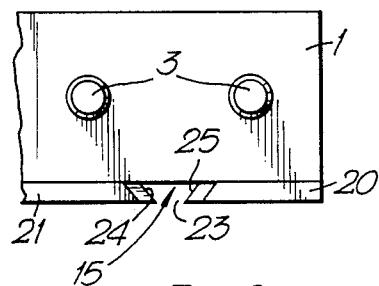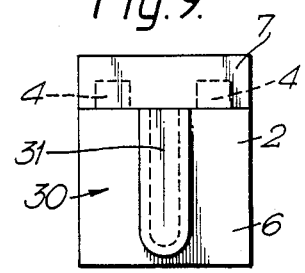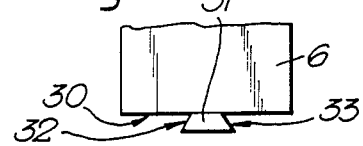

ANAESTHESIA EQUIPMENT

This invention relates to anaesthesia equipment and in particular to equipment including a rack on which various types of anaesthesia units such as vaporizers, gas flow monitors, gauges etc can be detachably mounted.

Examples of such equipment are described in GB Patent No 1385670 and GB Published Application No. 2193642A. As disclosed in these specifications, the various types of anaesthesia units are detachably and possibly interchangeably mounted on a rack in the form of a horizontal bar by means of mating elements comprising pairs of spigots and sockets. The mating elements not only serve to retain each unit in the rack but also provide a connection to a gas supply housed within the rack.

Figure 1:
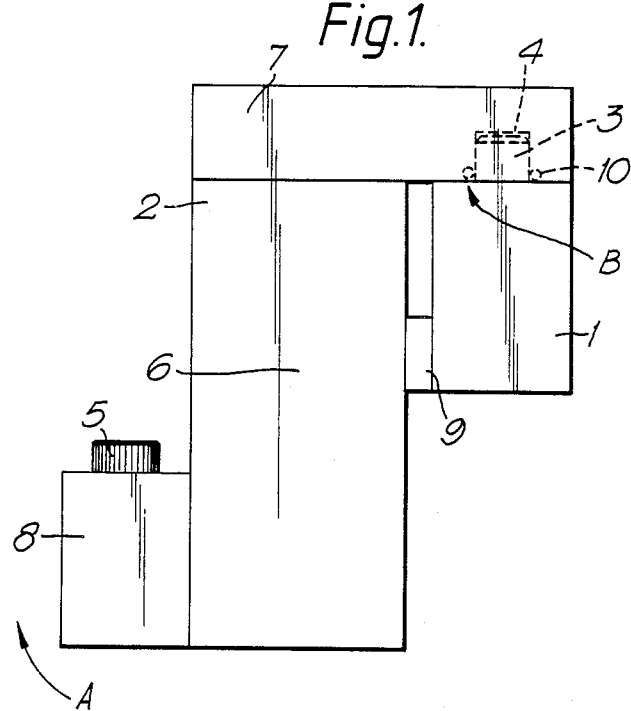

It has been found in practice that if the mating elements become slightly misaligned, e.g. because the unit is moved or tilted out of its upright position (as shown by the arrow A in FIG. 1) leakage of anaesthetic vapour or gas can take place from the mating elements (as shown at B in FIG. 1). This is disadvantageous since it means that the patient may not be receiving the correct supply and the operator may be adversely affected by the escaping vapour or gas.

It is an object of the present invention to provide anaesthesia equipment which reduces or prevents the occurrence of this unwanted escape.

In accordance with the invention, anaesthesia equipment comprises a mounting rack, an anaesthesia unit detachably mounted on said rack, connecting means comprising two mating elements, one associated with the rack and the other with the unit, enabling the unit to be mounted on the rack and connected to a fluid supply associated with the rack, and guide means located between the rack and the unit and associated with at least one of the rack and the unit to provide substantially accurate leak-free engagement of said mating elements.

The guide means may comprise cooperating elements, one of which is associated with the rack and the other with the unit.

Preferably the connecting means comprises two spigots and two sockets and the guide means is spaced apart from the line joining the two sockets or spigots.

The guide means may comprise a first member, for example an elongated pin or tongue mounted on either the unit or the rack and a second member cooperating with the first, for example an aperture, groove or slot on the rack or the unit respectively, the cooperating first and second members substantially preventing movement of the unit with respect to the rack in a generally horizontal direction, when the unit is mounted on the rack.

Figure 2:
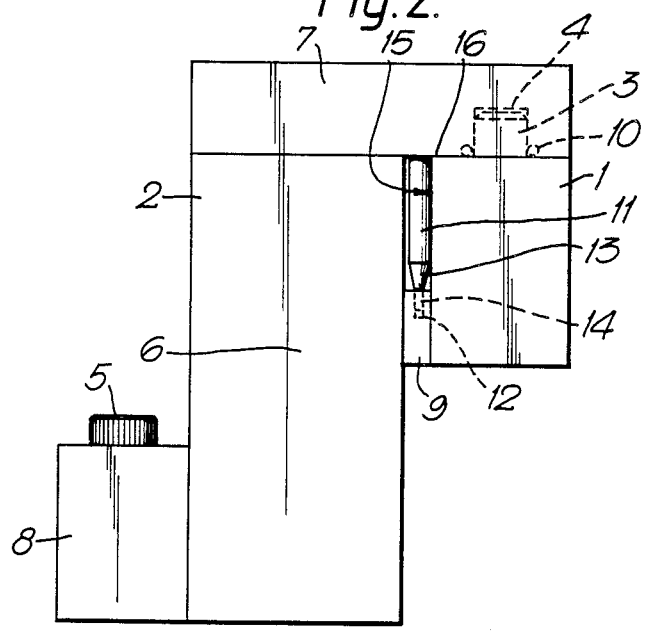

The axis of the first and second members of the guide means is preferably parallel to the axis of the spigots and sockets of the connecting means Three embodiments of the invention will now be described by way of example only with references to the accompanying drawings of which;

FIG. 1 is a diagrammatic side view of equipment comprising a rack and unit mounted thereon according to the prior art, FIG. 2 is a diagrammatic side view of equipment comprising a rack and unit mounted thereon in accordance with the first embodiment of the present invention, FIG. 3 is an exploded, simplified perspective view of the equipment shown in FIG. 2, FIG. 4 shows a partial perspective view of the rack of the second embodiment of the invention, FIG. 5 shows a partial front view in the direction of arrow A of the rack shown in FIG. 4, FIG. 6 shows a partial plan view in the direction of arrow B of the rack shown in FIG. 4, FIG. 7 shows a partial plan view in the direction of arrow B of a modified form of the rack shown in FIG. 4, FIG. 8 shows a partial plan view of the unit of the second embodiment of the invention, FIG. 9 shows a view of the rear of the unit shown in FIG. 8.

Figure 10:
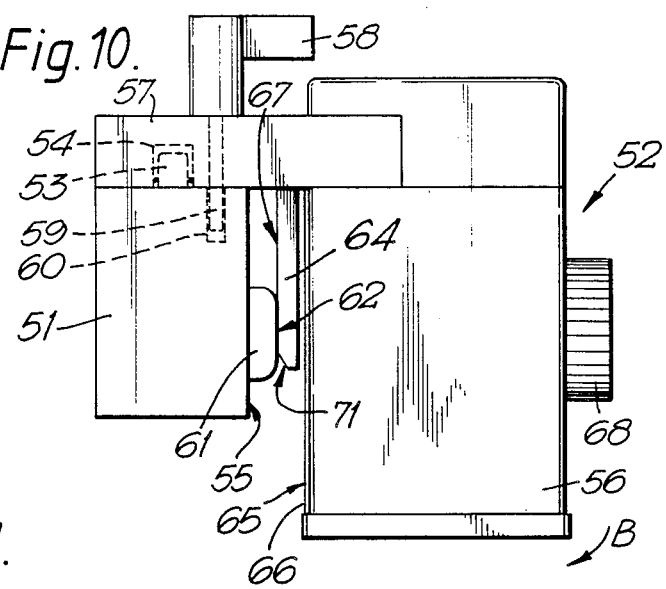
Figure 11:
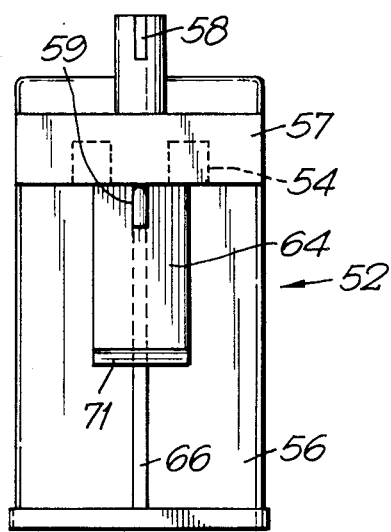
Figure 12:
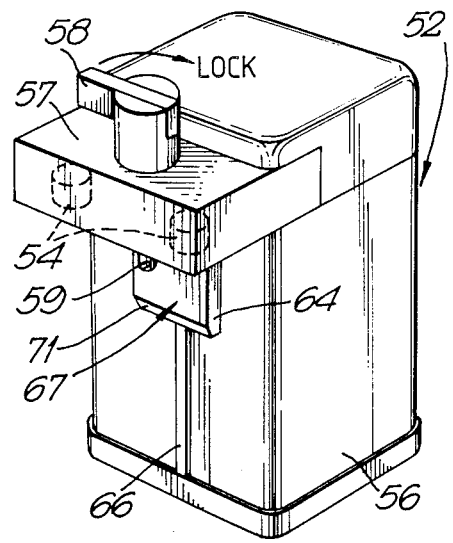

FIG. 10 shows a diagrammatic side view of equipment comprising a rack and unit mounted thereon in accordance with the third embodiment of the invention, FIG. 11 shows a rear view of the unit of the third embodiment of the invention, and, FIG. 12 shows a perspective view of the unit of the third embodiment of the invention.

As shown in FIGS. 1-3, anaesthesia equipment comprises a rack 1 in the form of a horizontal, generally rectangular cross-section bar and an anaesthesia unit 2, in this embodiment a vaporizer, detachably mounted on the rack by means of mating elements comprising a pair of spigots 3 on the rack engaging a pair of cooperating sockets 4 in the unit 2.

The unit 2 comprises a generally rectangular main body portion 6 and a top section 7, also generally rectangular. The top section 7 has a part extending rearwardly of the main body portion. The two sockets 4 are located on the underside of this rearwardly extending part. When the unit is mounted on the rack the rearwardly extending part is positioned above the top surface of the rack 1 as shown in FIGS. 1 and 2.

Although not shown in the drawings the unit incorporates appropriate pipework, valves and control means for controlling the concentration of anaesthetic vapour in the gas supplied from the rack 1. The control means is operated by means of a knob 5 mounted on the top surface of a small box 8 on the lower part of the front face of the main body portion 6. Other features such as an interlock device and anaesthetic concentration indicator may be incorporated.

The rack incorporates the pipework of a gas supply system which for the sake of clarity is not shown. The pipework of the gas supply system is connected to the internal pipework of the unit, also omitted from the drawings, by means of the spigots 3 and sockets 4. The rack has a small rectangular spacer bar 9 mounted on the lower part of its front face.

When the unit is mounted on the rack a good seal must be made between the interior of the sockets 4 and the exterior of the spigots 3 to prevent escape of gas and/or vapour from the equipment. The seal is usually conveniently in the form of an O-ring located within a groove (not shown) immediately adjacent the mouth of each socket 4. The O-ring engages the side surface of the cooperating spigot 3 when the unit 2 is mounted on the rack 1.

However, it has been found with the prior art equipment that in practice it is possible to tilt the unit forwardly and upwardly in the direction of the arrow A as shown in FIG. 1 causing a leak from the front of the O-ring seal at position B also shown in FIG. 1. Equally a downwards tilt in the opposite direction to arrow A may cause a leak from the rear portion of the O-ring seal.

The anaesthetic equipment according to the first embodiment of the present invention is constructed to reduce the likelihood of this leakage. As shown particularly in FIG. 2, the equipment incorporates a guide means comprising a pair of pins 11 and cooperating slots 12. The pins 11 are each secured to the underside of the top section 7 of the unit and extend in a downwards direction when the unit is in its operative position mounted on the rack 1. Each pin 11 is positioned so as to be located immediately in front of and in contact with the front face 15 of the rack 1 and engage a corresponding slot 12 formed in the top surface of the spacer bar 9.

Each pin 11 is generally rod-shaped and of circular cross-section. The lower extremity of each pin is shaped so as to have a part conical tapered section 13 and a generally cylindrical end tip 14 of smaller diameter than the main part of the pin. This shape has been found to be advantageous since as the unit is lowered into position the pin slides more readily over the top edge 16 of the front face 15 of the rack compared with a pin which was of constant cross-sectional diameter over the whole of its length.

As can be seen most clearly in FIG. 3 the slots 12 in the spacer bar 9 are elongated in the general direction of the length of the rack 1 and spacer bar 9. The width in the direction at right angles thereto is slightly greater than the diameter of the tip 14 of each pin 11. The two slots 12 are generally positioned in relation to the two spigots 3 so that they are generally at the four corners of a rectangle. This general arrangement together with the relative size of the pin tip and slot means that in use when the unit is mounted on the rack the engagement of the pin with the front face of the unit and of the tip with the side of its associated slot substantially prevents any sideways or tilting movement of the unit as experienced with prior art equipment.

As shown in FIGS. 4–9 the anaesthesia equipment according to the second embodiment of the invention comprises a rack 1 (shown particularly in FIGS. 4–7) and an anaesthesia unit 2 comprising a top section 7 and a main body portion 6. The unit 2 is attached to the rack 1 by means of spigots 3 on the rack mating with sockets 4 in the top section 7.

Attached to the front surface 15 of the rack 1 by means of screws or any other suitable means (not shown) are plates 20 and 21 spaced apart to define a vertical groove 23 therebetween. The edges 24, 25 of the plates adjacent this groove are undercut by being inclined so the groove has a "dove-tailed" configuration as is most clearly seen in FIG. 6. The lower part of the groove 23 has parallel sides whilst the upper part is opened out to form a wide mouth portion 26 by appropriate shaping of the edges 24, 25 of the plates 20, 21. The groove 23 thus has the overall general appearance of the letter 'Y'.

Attached to the rear surface 30 of the main body portion 6 of the unit 2 is a vertical tongue 31. The parallel side edges 32, 33 of the tongue are inclined so the tongue has a dove-tailed configuration of the vertical groove 23 between the plates 20, 21 on the rack 1. The lower extremity 34 of the tongue 31 is rounded.

In use the tongue 31 engages in the groove 23. The inclined surfaces 32, 33 on the tongue engage with the inclined surfaces 24, 25 and the outer surface 35 of the tongue engages the front surface 15 of the rack within the groove.

When fitting the unit 2 to the rack 1 the operator places the rounded lower extremity 34 of the tongue 31 within the mouth 26 of the groove 23 with the outer surface 35 of the tongue engaging the front surface 15 of the rack within the groove. The unit is then lowered. In doing so the parallel inclined edges 24, 25 of the groove engage the parallel side edges 32, 33 of the tongue so it slides vertically downwards. The sockets 4 engage the spigots 3 as the unit is lowered.

Since the inclined edges 32, 33 on the tongue 31 engage the inclined edges 24, 25 on the plates 20, 21, and the outer surface 35 of the tongue 31 contacts the front surface 15 of the rack, the unit is accurately located in the rack and the spigots accurately engage the sockets. Any tilting or other movement of the unit relative to the rack which would cause gas or vapour to escape from the seal between the sockets and spigots is substantially prevented.

Other forms of groove and tongue are possible. For example, as shown in FIG. 7 the plates 20, 21 may be shaped so that the edges 40, 41 of the groove are recessed and the groove has the general cross-sectional configuration of the letter 'T'. The tongue 31 on the rear of the unit 2 is correspondingly shaped to fit the vertical groove.

Alternatively the rear of the unit may be provided with a groove and the front of the rack with a corresponding tongue. More than one groove and corresponding tongue may be provided.

As shown in FIGS. 10, 11 and 12 the anaesthesia equipment according to the third embodiment of the invention comprises a rack 51 (shown in FIG. 10) and an anaesthesia unit 52 comprising a top section 57 and a main body portion 56. The unit 52 is provided with a control knob 68 for adjusting the vapour or gas flow as required and attached to the rack 51 by means of spigots 53 mating with sockets 54 in the top section 57. The unit is also provided with a locking mechanism comprising an operating lever 58 and a locking spindle 59 which cooperate with an aperture 60 in the rack to lock the unit in position once it has been located by means of the spigots in the sockets.

Attached to the front surface 55 of the rack by means of a screw or other suitable means (not shown) is a projection in the form of a plastics material button 61, the front face 62 of which is substantially flat and substantially vertical.

Attached to the underside of the top section 57 of the unit 52 is a downwardly extending tongue 64 of rectangular cross-section. The tongue is spaced apart from the rear surface 65 of the unit 52 by a distance slightly greater than the thickness of a vertically-extending folded seam weld 66 in the casing of the unit. The rear surface 67 of the tongue 64 i.e. that facing away from the unit is intended to engage and lie in juxtaposed relationship with the front surface 62 of the button 61 when the unit 52 is mounted on the rack, thereby preventing the unit from tilting out of position and thus causing an unwanted escape of gas or vapour from the connection between the spigots 53 and sockets 54. The lower part of the tongue 64 is formed with an inclined surface 71 to facilitate the positioning of the unit on the rack.

When fitting the unit 52 to the rack 51 the operator places the sockets 54 generally over the spigots 53 and the inclined surface 71 above the button 61 and then lowers the unit on to the rack. The engagement of the inclined surface 71 and the rear surface 67 of the tongue 64 with the button 61 guides the unit 52 into position on the rack 51 as shown in FIG. 10. The engagement of the rear surface 67 of the tongue 64 with the front face 62 of the button 61 maintains the unit in the required position on the rack and prevents tilting in the direction of the arrow C, thereby causing the unwanted escape of gas or vapour.

We claim:

1. Anaesthesia equipment comprising a mounting rack, an anaesthesia unit detachably mounted on said rack, connecting means comprising two mating elements, one associated with a first surface of the rack and the other with a first surface of the unit, enabling the unit to be mounted on the rack and connected to a fluid supply associated with the rack, the two said first surfaces facing one another when the unit is mounted on the rack, and guide means located between a second surface of the rack and a second surface of the unit when the unit is mounted on the rack, the guide means being associated with at least one of the rack and the unit to provide substantially accurate leak-free engagement of said mating elements said second surfaces of the rack and unit being substantially perpendicular to the first surfaces of the rack and unit respectively.

2. Anaesthesia equipment according to claim 1 wherein the guide means comprises cooperating elements, one of which is associated with the rack and the other with the unit.

3. Anaesthesia equipment according to claim 1 wherein the connecting means comprises two spigots and two sockets.

4. Anaesthesia equipment according to claim 3 wherein the guide means is spaced apart from the line joining the two sockets or two spigots.

5. Anaesthesia equipment according to claim 1 wherein the guide means comprises a first member mounted in either the unit or the rack and a second member cooperating with the first on the rack or unit respectively, the cooperating first and second members substantially preventing movement of the unit with respect to the rack in a generally horizontal direction, when the unit is mounted on the rack.

6. Anaesthesia equipment according to claim 5 wherein the first member comprises a elongated pin or tongue and the second member comprises a cooperating projection, aperture, groove or slot.

7. Anaesthesia equipment according to claim 5 wherein the lower extremity of the first member is narrower than the remainder thereof.

8. Anaesthesia equipment according to claim 6 wherein the first member engages the second surface of the rack when the unit is mounted thereon.

9. Anaesthesia equipment according to claim 1 wherein the said first surface of the rack is a horizontal top surface thereof, and said second surface of the rack is a vertical front surface.

* * * * *